(12) United States Patent
Taylor

(10) Patent No.: US 7,850,716 B2
(45) Date of Patent: Dec. 14, 2010

(54) ADJUSTABLE INTERCONNECTION DEVICE

(75) Inventor: Harold Sparr Taylor, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1033 days.

(21) Appl. No.: 11/357,767

(22) Filed: Feb. 17, 2006

(65) Prior Publication Data

US 2007/0233067 A1 Oct. 4, 2007

(51) Int. Cl.
A61B 17/84 (2006.01)
A61B 17/86 (2006.01)
A61B 17/58 (2006.01)
A61B 17/70 (2006.01)

(52) U.S. Cl. .............. 606/246; 606/60; 606/86 A; 606/279; 606/300; 606/301; 606/305; 606/306; 606/309; 606/320

(58) Field of Classification Search ............ 606/60, 606/61, 73, 86 A, 246–265, 279, 914
See application file for complete search history.

(56) References Cited

U.S. PATENT DOCUMENTS

| | | | |
|---|---|---|---|
| 5,207,678 A | 5/1993 | Harms | |
| 5,575,792 A | 11/1996 | Errico | |
| 5,609,593 A | 3/1997 | Errico | |
| 5,609,654 A | 3/1997 | Le et al. | |
| 5,630,817 A * | 5/1997 | Rokegem et al. ............ 606/269 |
| 5,643,263 A | 7/1997 | Simonson | |
| 5,797,911 A | 8/1998 | Sherman | |
| 5,885,285 A | 3/1999 | Simonson | |
| 5,947,967 A * | 9/1999 | Barker ................. 606/278 |
| 6,074,391 A | 6/2000 | Metz-Stavenhagen | |
| 6,280,442 B1 | 8/2001 | Barker | |
| 6,520,962 B1 | 2/2003 | Taylor | |
| 6,562,038 B1 | 5/2003 | Morrison | |
| 6,572,618 B1 | 6/2003 | Morrison | |
| 6,579,292 B2 | 6/2003 | Taylor | |
| 6,648,887 B2 | 11/2003 | Ashman | |
| 6,685,705 B1 | 2/2004 | Taylor | |
| 6,755,830 B2 * | 6/2004 | Minfelde et al. ............ 606/278 |
| 6,872,209 B2 | 3/2005 | Morrison | |
| 7,066,939 B2 | 6/2006 | Taylor | |
| 2005/0159750 A1 * | 7/2005 | Doherty ................. 606/73 |

FOREIGN PATENT DOCUMENTS

FR 2 827 757 A 1/2003
JP 2001-252283 A 9/2001

* cited by examiner

Primary Examiner—Thomas C Barrett
Assistant Examiner—Sameh Boles

(57) ABSTRACT

Mechanisms for connecting an elongated member for orthopedic support or therapy to bone or other tissue are disclosed. Embodiments may include a receiver member with a channel for accommodating an elongated member such as a spinal rod and a channel for accommodating a bone-engaging member, a bone-engaging member that is insertable into the channel in the receiver member, and a lock member for locking the receiver member, bone-engaging member, and elongated member together. The channels may be variously oriented with respect to each other. Methods for using such embodiments are also disclosed.

31 Claims, 4 Drawing Sheets

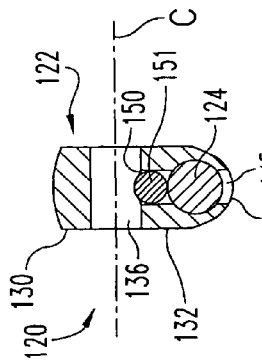
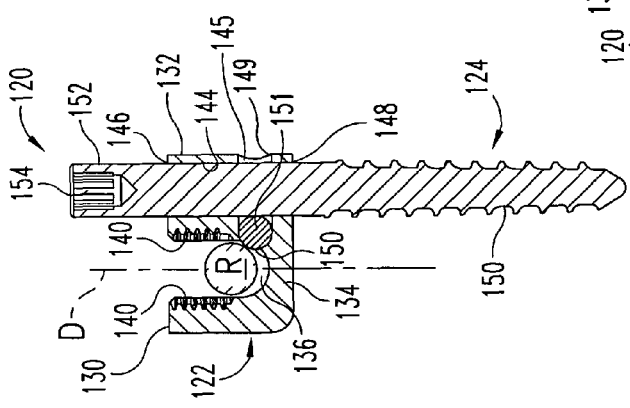
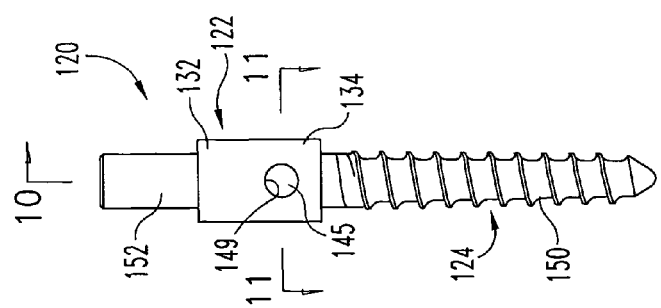
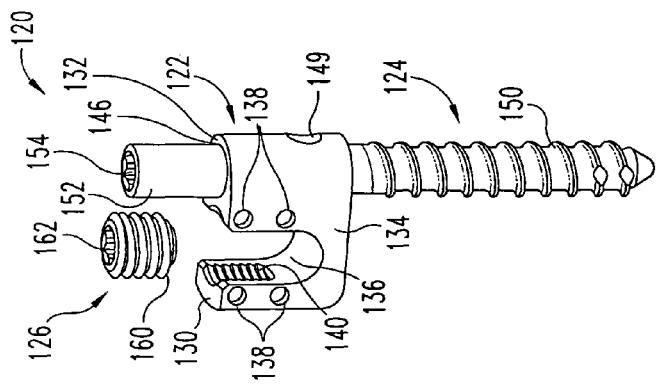

ADJUSTABLE INTERCONNECTION DEVICE

The present disclosure generally concerns mechanisms used to connect orthopedic implants with elongated members, such as rods, for therapeutic or corrective purposes.

BACKGROUND

In the field of orthopedic surgery, several types of apparatus are known for correction, support or other treatment of tissues. For example, in the spinal field, elongated support members such as rods, bars or plates are connected to vertebrae or adjacent tissue so as to provide a corrected spinal curvature, for support of injured or surgically-treated vertebrae or vertebral joints, and for other purposes. Such elongated members can be connected to bone, for example, via a variety of implants including screws, bolts, clamps, wires, hooks.

In some surgical cases, it may be desired to have the elongated member positioned at different heights from bone or other tissue, or have the ability to adjust the positioning of the elongated member or a piece that holds it with respect to a screw, hook or other apparatus. The surgical therapy, the size of the patient and/or the anatomy to be operated on may require variability of placement and/or adjustment of implants with respect to elongated members.

BRIEF DESCRIPTION OF THE DRAWINGS

FIG. 8 is a partially exploded perspective view of an embodiment of an orthopedic implant.

FIG. 9 is a side elevational view of the embodiment of FIG. 8.

FIG. 10 is a cross-sectional view, taken along the line 10-10 in FIG. 9 and viewed in the direction of the arrows, of the embodiment of FIG. 8, and including an elongated member.

FIG. 11 is a cross-sectional view, taken along the line 11-11 in FIG. 9 and viewed in the direction of the arrows, of the embodiment of FIG. 8.

DESCRIPTION OF THE ILLUSTRATED EMBODIMENTS

Figure 1:
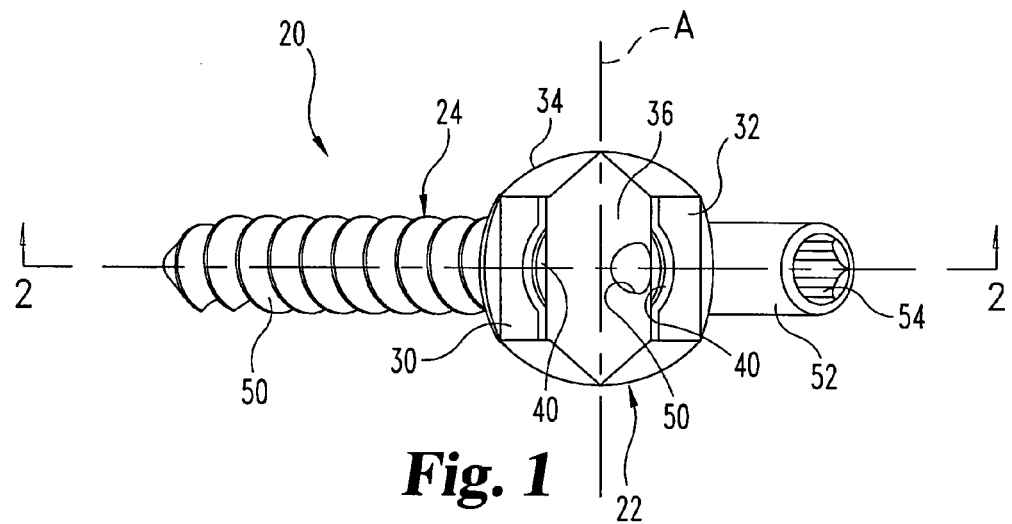
FIG. 1 is a top plan view of an embodiment of an orthopedic implant.
Figure 2:
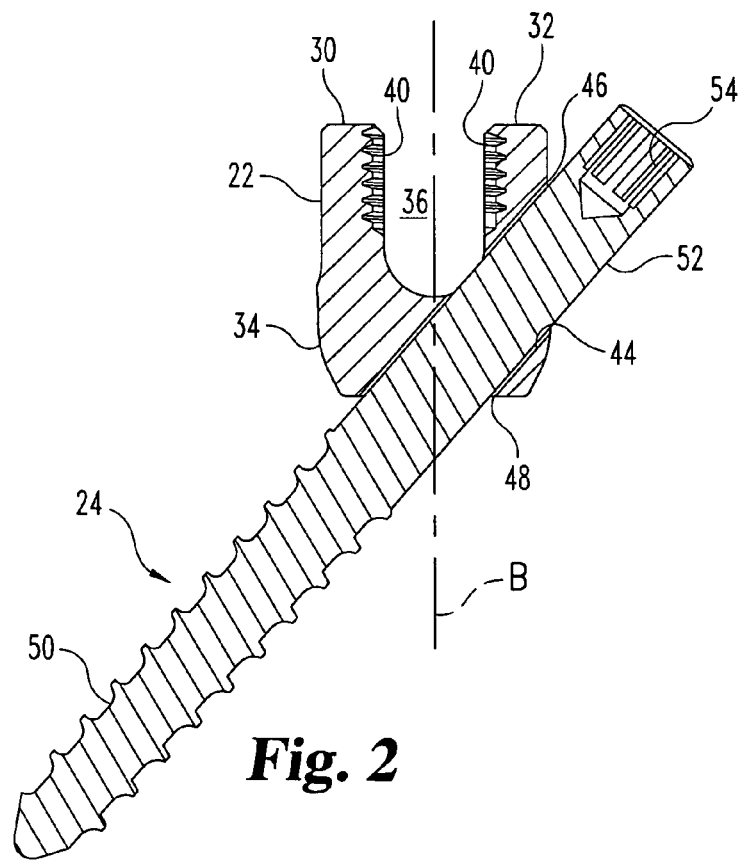
FIG. 2 is a cross-sectional view, taken along the line 2-2 in FIG. 1 and viewed in the direction of the arrows, of the embodiment of FIG. 1.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated devices, and such further applications of the principles of the disclosure as illustrated therein, being contemplated as would normally occur to one skilled in the art to which the disclosure relates.

Referring now generally to FIGS. 1-7, an embodiment of an implant 20 is shown. In that embodiment, implant 20 includes a receiver member 22, a bone-engaging member 24, and a lock member 26. In general, implant 20 is connected to bone or other tissue and to a support member, such as a rod, bar or other elongated member, so that the support member can provide correction, support or other benefit to an orthopedic surgical site such as a part of the spinal column.

Receiver member 22 includes two branches 30, 32 that extend from a base portion 34, and that at least partially define a channel 36 for accommodating an elongated member such as an orthopedic rod. In this embodiment, receiver member 22 may be considered substantially U-shaped. Channel 36 has a longitudinal axis A substantially along or parallel to which an elongated member can lie. The illustrated embodiment of receiver member 22 shows branches 30, 32 extending generally upward or away from base portion 34 and the tissue, such as a vertebra, to which receiver member 22 is connected, but in other embodiments branches 30, 32 could be otherwise oriented, e.g. sloped or slanted with respect to base portion 34 and/or to a vertebral surface or other tissue. In such embodiments, channel 36 could open somewhat or entirely to the side of base portion 34. Branches 30, 32 are also shown generally parallel to each other and somewhat planar, and in other embodiments could be non-parallel with each other and/or curved. In the illustrated embodiment, branches 30, 32 each have an internal thread 40 communicating with channel 36.

Receiver member 22 further includes a channel 44 in which at least a part of bone-engaging member 24 can be placed. In this embodiment, channel 44 is substantially cylindrical and has a diameter approximately equal to or slightly larger than the diameter of bone-engaging member 24. Channel 44 ends in an opening 46 in a side of branch 32 and an opening 48 in a bottom surface of base portion 34, and therefore in this embodiment channel 44 is sloped or slanted with respect to channel 36. Put differently, in this embodiment channel 44 is oblique to an axis B (also referred to herein as a "vertical" axis) that is perpendicular to the longitudinal axis of channel 36 and parallel to branches 30, 32. Opening 46 is oblong, being the intersection between a plane (branch 32) and a cylinder (channel 44) that is not perpendicular to the plane. For similar reasons, opening 48 is also oblong, and in this embodiment is in a plane substantially perpendicular to axis B. In the illustrated embodiment, channel 44 intersects or communicates with channel 36 at an opening 50.

In other embodiments, channel 44 could be differently configured. For example, channel 44 could be substantially perpendicular to axis A. In such a case, channel 44 could be substantially in base portion 34 (i.e. beneath channel 36 in the embodiment shown in FIG. 1) and orthogonal to axes A and B, or substantially in one of branches 30, 32 (i.e. beside channel 36 in the embodiment shown in FIG. 1) and parallel to axis B. It will be seen that openings would be provided in the sides of base portion 34 and perhaps in portions of branches 30 and/or 32 in the example where channel 44 is substantially in base portion 34, and in a top portion of one branch and through the bottom of base portion 34 in the example where channel 44 is substantially in that particular branch.

Figure 7:
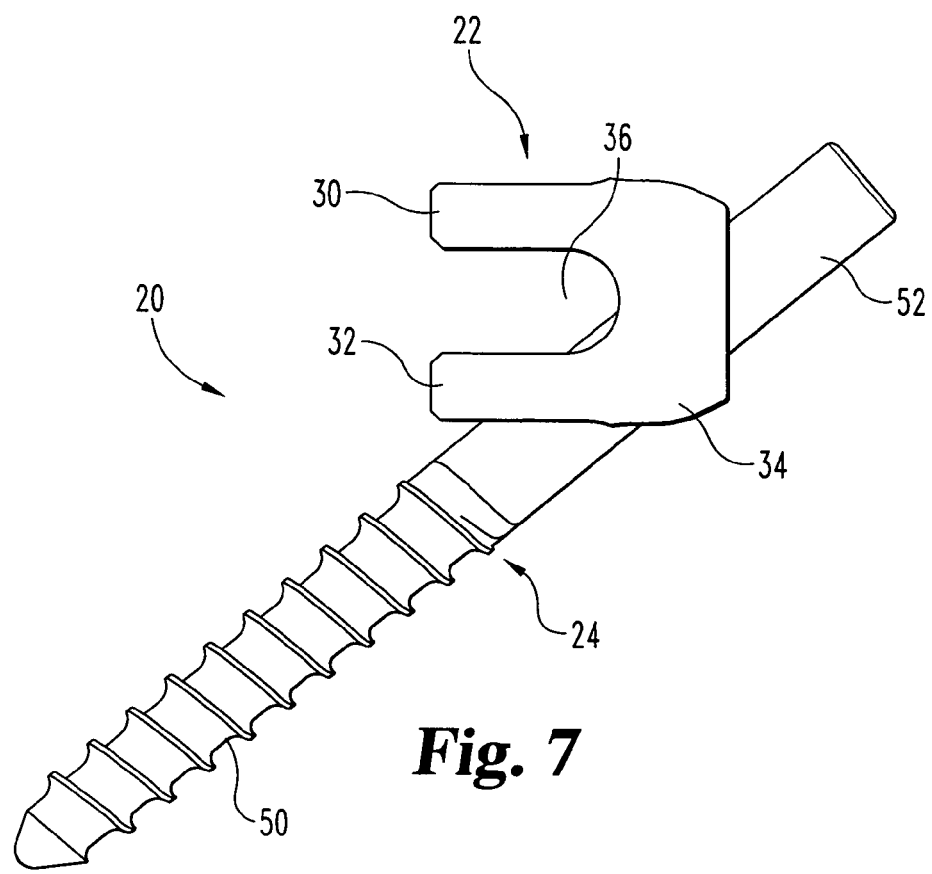
FIG. 7 is a side elevational view of the embodiment of FIG. 1 in a different orientation.

As seen in FIG. 7, receiver member 22 may be placed on bone-engaging member 24 so that branch 32 is relatively close to bone or other tissue, rather than base portion 34. In contradistinction to the embodiment illustrated in FIG. 1 and described above, in which shaft portion 52 of bone-engaging member 24 is inserted through opening 48 in base portion 34 and may extend from opening 46 in branch 32, in FIG. 7 shaft 52 of bone-engaging member 24 is inserted through opening 46 in branch 32 and may extend from opening 48 in base 34. Thus, configured as in FIG. 1 base portion 34 of receiver member 22 generally faces tissue into or through which bone-engaging member 24 extends, and configured as in FIG. 7 branch 32 of receiver member 22 generally faces such tissue. This use of the illustrated embodiment of receiver member 22 and bone-engaging member 24 may be indicated in cases where the elongated member is desired to reside quite close to bone or other tissue, in cases in which the surgical situation and/or anatomy is such that insertion of the elongated member from a relative side direction rather than a relative top direction is indicated, or in other cases in which the surgeon determines that such positioning is desirable.

Bone-engaging member 24, in the illustrated embodiment, is a bone screw having a threaded lower portion 50 and a substantially cylindrical upper shaft portion 52. Shaft portion 52 and bone-engaging portion 50 are integral with each other in the illustrated embodiment, and are substantially collinear with a central longitudinal axis of bone-engaging member 24. Upper shaft portion 52 has a diameter, and in a particular embodiment the crest diameter of lower portion 50 is approximately the same as the diameter of upper portion 52. In other embodiments, the threads could be differently configured, such as having a crest diameter larger than the diameter of upper portion 52 and at least slightly smaller than the diameter of channel 44 of receiver member 22. An internal print 54 (e.g. a hexagonal print) is provided in this embodiment of bone-engaging member 24 for a turning or holding tool (not shown), although an external print, driving flats or other type of driving or gripping surface(s) could be provided at one or more points along shaft portion 52. If an external print or other surface is provided, it may be configured so that its diameter does not exceed that of the rest of shaft portion 52, or so that its diameter does not exceed the diameter of channel 44 of receiver member 22. In other embodiments, threaded lower portion 50 could be replaced with a hook-shaped portion, a clamp portion, or other apparatus for connecting bone-engaging member 24 to bone or other tissue. The threads of the illustrated embodiment of lower portion 52 may be configured for good purchase in cancellous or other types of bone, and may be cannulated or include holes through portion 52 perpendicular or oblique to its axis for bone ingrowth.

The illustrated embodiment of lock member 26 is a set screw having an external threaded portion 60 and an internal driving print 62. Print 62 may be a hexagonal or hexalobed opening, or may be otherwise configured. In other embodiments, lock member 26 may be provided with a head portion with an internal and/or external print. In such cases, lock member 26 may be torque-limiting, so that such head portion separates from a threaded portion on application of sufficient torque. In yet other embodiments, lock member 26 could be a clamp, spring-loaded, ratcheting, or other type of member that connects with receiver member 22.

In use, implant 20 is introduced into a surgical site and connected to tissue. In the following discussion, spinal surgery will be described, although similar orthopedic surgical steps could be taken at other surgical sites. With the illustrated embodiment, a hole is drilled into a bone (e.g. a vertebra), which may then be tapped. The orientation of the hole with respect to the bone and/or to other tissue may be determined at least in part by the relative angle of channel 44 in receiver member 22 to its elongated member channel 36. For example, a surgeon will orient the hole in the bone so that when bone-engaging member 24 is in the hole and at least partially within channel 44 of receiver member 22, receiver member 22 can be rotated around bone-engaging member 24 so that channel 36 is directed along a desired direction. In many instances of spinal surgery, for instance, channel 36 should be directed substantially along a portion of the spinal column or vertebral segment, and thus a hole for bone-engaging member 24 should be made in tissue so that when receiver member 22 is placed on bone-engaging member 24, channel 36 can be so directed.

Bone-engaging member 24 is threaded into the hole to a desired depth, which may be determined by the amount of member 24 desired to be within the bone, the amount desired to be exposed from the bone, and/or other considerations. When bone-engaging member 24 is placed as the surgeon desires, receiver member 22 is placed on bone-engaging member 24 by inserting shaft portion 52 into channel 44. In the illustrated embodiment, a portion of bone-engaging member 24 occupies a portion of channel 36 of receiver member 22 through opening 50. Receiver member 22 can be adjusted with respect to bone-engaging member 24 in 360 degrees of rotation (e.g. around the longitudinal axis of member 24) and to any of an infinite number of positions along member 24. That is, receiver member 22 can be placed at any location along member 24, in the illustrated embodiment, between the point where receiver member 22 contacts bone or other tissue, and the point where member 24 is not in opening 50 and channel 36. Such adjustments may be made during and/or after original placement of receiver member 22 on bone-engaging member 24. In certain embodiments, bone-engaging member 24 may protrude from opening 46, and in other embodiments the top of shaft portion 52 of bone-engaging member 24 could be below the surface of opening 46 and within receiver member 22.

Figure 3:
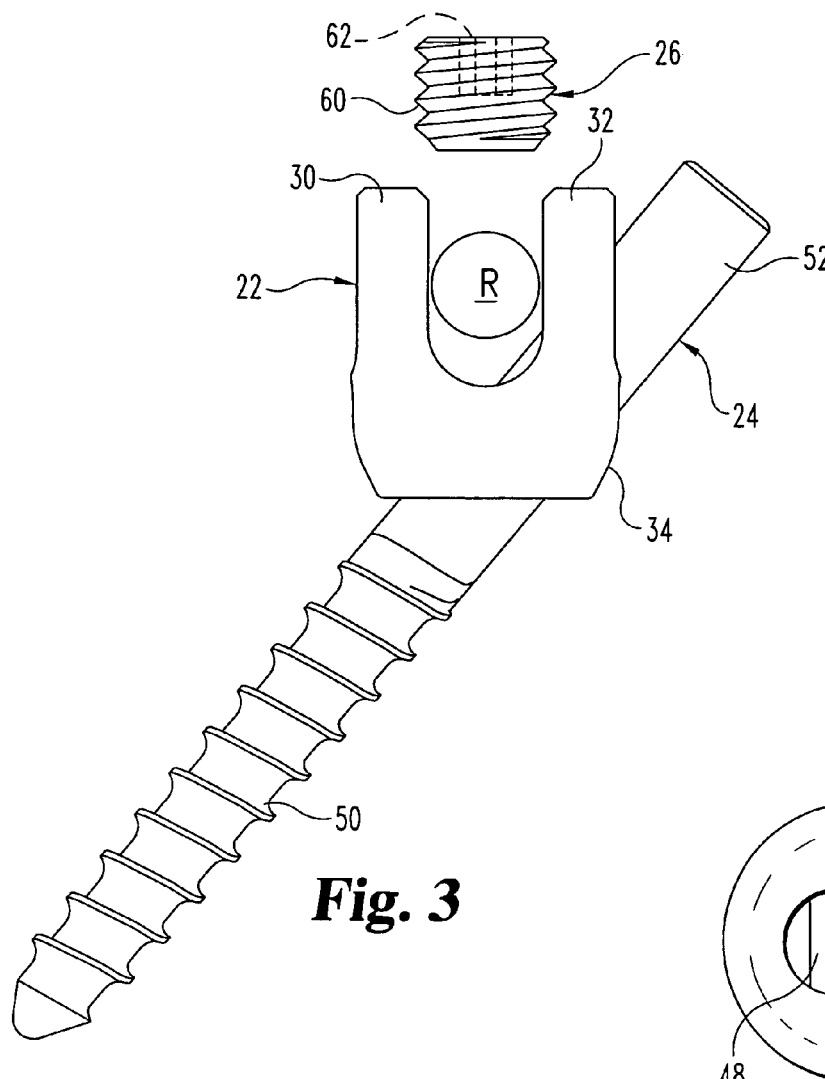
FIG. 3 is a partially exploded side elevational view of the embodiment of FIG. 1, including an embodiment of an elongated member and a locking member.
Figure 4:
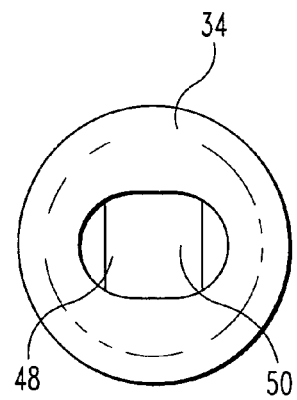
FIG. 4 is a bottom plan view of an embodiment of a receiver member included in the embodiment of FIG. 1.
Figure 5:
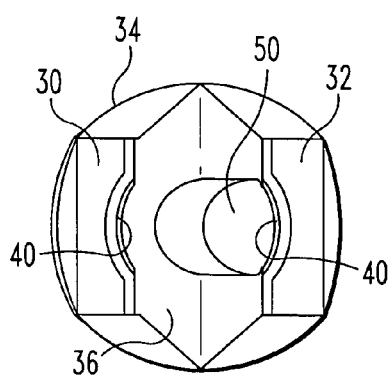
FIG. 5 is a top plan view of the embodiment of FIG. 4.
Figure 6:
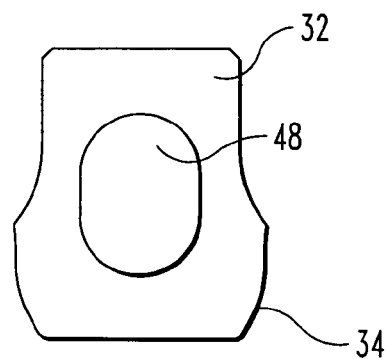
FIG. 6 is a side elevational view of the embodiment of FIG. 4.

An elongated member, such as spinal rod R shown in FIG. 3, is placed at least partially in channel 36. The elongated member, which may be a rod, bar, or similar item, can be pre-bent to conform to a particular spinal curvature or as a particular correction, support or therapy requirement may dictate, or the elongated member can be bent in situ. Placement and bending of an elongated member may occur prior to locking receiver member 22 with respect to bone-engaging member 24 so that the adjustability of receiver member 22 with respect to bone-engaging member 24 can be used to ease such placement, bending, and/or other configuration or manipulation of the implant system. An elongated member may be placed in channel 36 of receiver member 22 after receiver member 22 is placed on bone-engaging member 24, or an elongated member could be placed in channel 36 prior to placing receiver member 22 on bone-engaging member 24.

When receiver member 22 and bone-engaging member 24 are assembled and an elongated member is at least partially in channel 36 of receiver member 22, and any adjustments the surgeon deems necessary or prudent are made, lock member 26 is engaged to receiver member 22 to lock together receiver member 22, the elongated member, and bone-engaging member 24. In the illustrated embodiment, in which lock member 26 is a set screw, lock member 26 can be threaded into internal threads 40 in branches 30, 32 of receiver member 22. Tightening lock member 26 into contact with the elongated member to a desired degree presses the elongated member into channel 36 and against the portion of bone-engaging member 24 exposed in opening 50, transmitting force or pressing bone-engaging member 24 against the wall of channel 44. The elongated member, receiver member 22 and bone-engaging member 24 are thus locked with respect to each other. Similar steps may be taken to implant additional units of implant 20 or other types of orthopedic implant, if deemed necessary or prudent by the surgeon to accomplish the treatment, correction or other goals of the surgery.

Referring now generally to FIGS. 8-11, there is shown an embodiment of an implant 120. Implant 120 includes a receiver portion 122, a bone-engaging member 124 that is essentially identical in the illustrated embodiment to bone-engaging member 24, and a lock member 126. In general, implant 120 is connected to bone or other tissue and to a support member, such as a rod, bar or other elongated member, so that the support member can provide correction, support or other benefit to an orthopedic surgical site such as a part of the spinal column.

Receiver member 122 includes two branches 130, 132 that extend from a base portion 134, and that at least partially define a channel 136 for accommodating an elongated member such as an orthopedic rod. In this embodiment, receiver member 122 may be considered substantially U-shaped. Channel 136 has a longitudinal axis C substantially along or parallel to which an elongated member can lie. The illustrated embodiment of receiver member 122 shows branches 130, 132 extending generally upward or away from base portion 134 and the tissue, such as a vertebra, to which receiver member 122 is connected, but in other embodiments branches 130, 132 could be otherwise oriented, e.g. sloped or slanted with respect to base portion 134 and/or to a vertebral surface or other tissue. In such embodiments, channel 136 could open somewhat or entirely to the side of base portion 134. Branches 130, 132 are also shown generally parallel to each other and somewhat planar, and in other embodiments could be non-parallel with each other and/or curved. Receiver member 122 may also have one or more indentations 138 in one or both of branches 130, 132 and/or on either side of branches 130, 132 for receiving part of a holding or manipulating tool (not shown). In the illustrated embodiment, branches 130, 132 each have an internal thread 140 communicating with channel 136.

Receiver member 122 further includes a channel 144 in which at least a part of bone-engaging member 124 can be placed, and an aperture 145 that communicates with channel 144 and channel 136. In the illustrated embodiment, channel 144 is substantially cylindrical and has a diameter approximately equal to or slightly smaller than the diameter of bone engaging member 124. Channel 144 is substantially parallel to an axis D (also referred to herein as a "vertical" axis) perpendicular to axis C and extends through branch 132, thus being offset from channel 136 in this embodiment. Channel 144 forms an opening 146 in the top of branch 132 and an opening 148 in a bottom of base portion 134. Openings 146 and 148 are substantially circular in the illustrated embodiment, as they are the intersection between plane (top of branch 132 and bottom of base portion 134) and a cylinder (channel 144) that is substantially perpendicular to those planes. In the illustrated embodiment, aperture 145 is substantially cylindrical and extends through branch 132 and forms an opening 149 at the exterior of branch 132 and an opening 150 that communicates with channel 136 and has a somewhat smaller diameter than aperture 145 and opening 149. A spherical ball or other force-transmitting member 151, is placed in aperture 145, and when receiver member 122 and bone-engaging member 124 are assembled together, ball 151 is between bone-engaging member 124 and channel 136.

In other embodiments, channel 144 and/or aperture 145 could be differently configured. For example, channel 144 could be substantially perpendicular to axis C. In such a case, channel 144 could be substantially in base portion 134 (i.e. beneath channel 136 in the embodiment shown in FIG. 8) and orthogonal to axes C and D. As another example, channel 144 could be angled with respect to channel 136 and through the side of branch 132 and base 134, e.g. oblique to axis D, as disclosed above with respect to channel 44 of the illustrated embodiment of receiver member 22. It will be seen that openings would be provided in the sides of base portion 134 and perhaps in portions of branches 130 and/or 132 in the example where channel 144 is substantially in base portion 134, and in a side of one branch and through the bottom of base portion 34 in the example where channel 44 is obliquely angled. Aperture 145 can be differently oriented, if necessary, to maintain member 151 between bone-engaging member 124 and channel 136 when bone-engaging member 124 and receiver member 122 are assembled. Further, regardless of the orientation of channel 144, aperture 145 could be alternatively shaped. For example, instead of a cylinder, aperture 145 could be a slot through receiver member 122, and instead of a ball-shaped member 151, a cylinder or pin having a length less than or equal to the width of the slot could be placed in the slot so as to be between bone-engaging member 124 and channel 136.

Bone-engaging member 124, in the illustrated embodiment, is a bone screw having a threaded lower portion 150 and a substantially cylindrical upper shaft portion 152. Upper shaft portion 152 has a diameter, and in a particular embodiment the crest diameter of lower portion 150 is approximately the same as the diameter of upper portion 152. In other embodiments, the threads could be differently configured, such as having a crest diameter larger than the diameter of upper portion 152 and at least slightly smaller than the diameter of channel 144 of receiver member 122. An internal print 154 (e.g. a hexagonal print) is provided in this embodiment of bone-engaging member 124 for a turning or holding tool (not shown), although an external print, driving flats or other type of driving or gripping surface(s) could be provided at one or more points along shaft portion 152. If an external print or other surface is provided, it may be configured so that its diameter does not exceed that of the rest of shaft portion 152, or so that it does not exceed diameter of channel 144 of receiver member 122. In other embodiments, threaded lower portion 150 could be replaced with a hook-shaped portion, a clamp portion, or other apparatus for connecting bone-engaging member 124 to bone or other tissue. The threads of the illustrated embodiment of lower portion 152 may be configured for good purchase in cancellous or other types of bone, and may be cannulated or include holes through portion 152 perpendicular or oblique to its axis for bone ingrowth.

The illustrated embodiment of lock member 126 is a set screw with an external threaded portion 160 and an internal driving print 162. Print 162 may be a hexagonal or hexalobed opening, or may be otherwise configured. In other embodiments, lock member 126 may be provided with a head portion with an internal and/or external print. In such cases, lock member 126 may be torque-limiting, so that such head portion separates from a threaded portion on application of sufficient torque. In yet other embodiments, lock member 126 could be a clamp, spring-loaded, ratcheting, or other type of member that connects with receiver member 122.

In use, implant 120 is introduced into a surgical site and connected to tissue. In the following discussion, spinal surgery will be described, although similar orthopedic surgical steps could be taken at other surgical sites. With the illustrated embodiment, a hole is drilled into a bone (e.g. a vertebra), which may then be tapped. The orientation of the hole with respect to the bone or other tissue may be determined at least in part by the relative angle of channel 144 in receiver member 122 to its elongated member channel 136. For example, a surgeon will orient the hole in the bone so that when bone-engaging member 124 is in the hole and at least partially within channel 144 of receiver member 122, receiver member 122 can be rotated around bone-engaging member 124 so that channel 136 is directed along a desired direction. In many instances of spinal surgery, for instance, channel 136 should be directed substantially along a portion of the spinal column or vertebral segment, and thus a hole for bone-engaging member 124 should be made in tissue so that when receiver member 122 is placed on bone-engaging member 124, channel 136 can be so directed.

Bone-engaging member 124 is threaded into the hole to a desired depth, which may be determined by the amount of member 124 desired to be within the bone, the amount desired to be exposed from the bone, and/or other considerations. When bone-engaging member 124 is placed as the surgeon desires, receiver member 122 is placed on bone-engaging member 124 by inserting shaft portion 152 into channel 144. Bone-engaging member 124 is adjacent to or abuts ball 151 when placed in channel 144. Receiver member 122 can be adjusted with respect to bone-engaging member 124 in 360 degrees of rotation (e.g. around the longitudinal axis of member 124) and to any of an infinite number of positions along member 124. That is, receiver member 122 can be placed at any location along member 124, in the illustrated embodiment, between the point where receiver member 122 contacts bone or other tissue, and the point where member 124 is not adjacent to or abutting ball 151 in aperture 145. Such adjustments may be made during and/or after original placement of receiver member 22 on bone-engaging member 24. In certain embodiments, bone-engaging member 124 may protrude from opening 146, and in other embodiments the top of shaft portion 152 of bone-engaging member 124 could be below the surface of opening 146 and within receiver member 122.

An elongated member, such as spinal rod R shown in FIG. 10, is placed at least partially in channel 136. The elongated member, which may be a rod, bar, or similar item, can be pre-bent to conform to a particular spinal curvature or as a particular correction, support or therapy requirement may dictate, or the elongated member can be bent in situ. Placement and bending of an elongated member may occur prior to locking receiver member 122 with respect to bone-engaging member 124 so that the adjustability of receiver member 122 with respect to bone-engaging member 124 can be used to ease such placement, bending, and/or other configuration or manipulation of the implant system. An elongated member may be placed in channel 136 of receiver member 122 after receiver member 122 is placed on bone-engaging member 124, or an elongated member could be placed in channel 136 prior to placing receiver member 122 on bone-engaging member 124.

When receiver member 122 and bone-engaging member 124 are assembled and an elongated member is at least partially in channel 136 of receiver member 122, and any adjustments the surgeon deems necessary or prudent are made, lock member 126 is engaged to receiver member 122 to lock together receiver member 122, the elongated member, and bone-engaging member 124. In the illustrated embodiment, in which lock member 126 is a set screw, lock member 126 can be threaded into internal threads 140 in branches 130, 132 of receiver member 122. Tightening lock member 126 into contact with the elongated member to a desired degree presses the elongated member into channel 136 and against the portion of ball 151 exposed in opening 150, and ball 151 presses (or transmits the force to) bone-engaging member 124 against the wall of channel 144. The elongated member, receiver member 122 and bone-engaging member 124 are thus locked with respect to each other. Similar steps may be taken to implant additional units of implant 120 or other types of orthopedic implant, if deemed necessary or prudent by the surgeon to accomplish the treatment, correction or other goals of the surgery.

It will be seen that multiple units of implants 20 and/or 120 can be used with one or more elongated members in an orthopedic support or treatment apparatus. Further, one or more units of implants 20 and/or 120 may be used with other types of orthopedic implant in such an apparatus. The apparatus disclosed herein may be included in a kit that includes one or more receiver members, one or more bone-engaging members, one or more lock members, and/or other implantable orthopedic devices. Where multiple receiver members are included in such a kit, they may be of different overall size, they may be compatible with various sizes or types of elongated member or bone-engaging member, and/or they may have different orientations of a channel for a bone-engaging member. Where multiple bone-engaging members are included in such a kit, they may be of different lengths and/or diameters, and they may be of different types (e.g. screws, hooks, clamps, etc.). Where multiple lock members are included in such a kit, they may be of different lengths and/or diameters as different receiver members and/or elongated members may require, and they may be of different types (e.g. headed screws, break-off screws, clamps, etc.).

Thus, the illustrated embodiments of implants 20, 120 have a locked condition in which an elongated member is held within a receiver member 22, 122, which is substantially immobile with respect to a bone-engaging member 24, 124 that is attached or connected to bone or other tissue. The illustrated embodiments of implants 20, 120 further have an unlocked condition in which receiver member 22, 122 is placed on bone-engaging member 24, 124 and is rotatable with respect to bone-engaging member 24, 124 at least substantially around a longitudinal axis of bone-engaging member 24, 124, or to such a degree as may be permitted by the configuration of channel 44, 144 of receiver member 22, 122. In the unlocked condition, receiver member 22, 122 is also slidable or otherwise movable along the length of bone-engaging member 24, 124 and channel 44, 144 of receiver member 22, 122. Receiver member 22, 122 and bone-engaging member 24, 124 are accordingly rotationally adjustable and adjustable in a linear direction. That linear direction may be substantially dorsal, posterior, lateral, or otherwise, depending on the orientation of bone-engaging member 24, 124.

Aspects disclosed with respect to implant 20, in many cases, may be incorporated into implant 120, and vice versa. For example, indentations 138 could be used in embodiments similar to implant 20. The devices of the present invention are preferably constructed of sturdy bio-compatible materials, such as stainless steel, titanium, certain plastics, or other known materials.

While the disclosure has been illustrated and described in detail in the drawings and foregoing description, the same is to be considered as illustrative and not restrictive in character, it being understood that only embodiments have been shown and described and that all changes and modifications that come within the spirit of the disclosure are desired to be protected.

What is claimed is:

1. An apparatus comprising:
    a receiver member extending along a vertical axis and having two branches each having a length extending along said vertical axis, a base portion, a first channel substantially between said branches and including an arcuate bottom surface for receiving an elongated member, a second channel for receiving a bone-engaging member and extending along said vertical axis and through one of said branches along said length from a top surface of said one of said branches to an opposite bottom surface of said base portion, said second channel being non-collinear with said first channel and having a longitudinal axis, and an opening extending transversely to said vertical axis through a portion of said arcuate bottom surface and between said first channel and said second channel;

a bone-engaging member having an engaging portion and a shaft portion that are substantially collinear, said shaft portion being at least partially within said second channel; and a lock member connected to said receiver member, wherein said apparatus has a locked condition in which said receiver member and said bone-engaging member are substantially immobile with respect to each other, and an unlocked condition in which said bone-engaging member and said receiver member are movable with respect to each other around and along said second channel to an infinite number of relative positions.

2. The apparatus of claim 1, further comprising an elongated member at least partially within said first channel of said receiver member, wherein in said locked condition said lock member presses against said elongated member and said elongated member transmits force to lock said bone-engaging member with respect to said receiver member.

3. The apparatus of claim 2, wherein said elongated member contacts said bone-engaging member directly.

4. The apparatus of claim 2, further comprising a force-transmitting member between said elongated member and said bone-engaging member.

5. The apparatus of claim 4, wherein said force-transmitting member is one of a ball and a pin.

6. The apparatus of claim 5, wherein said force-transmitting member comprises a spherical shaped ball.

7. The apparatus of claim 1, wherein said first channel has a longitudinal axis, said vertical axis is perpendicular to said axis of said first channel, and said axis of said second channel is oblique to said vertical axis.

8. The apparatus of claim 7, wherein said first channel and said second channel intersect, and when said bone-engaging member is within said second channel, a portion of said bone-engaging member is within said first channel.

9. The apparatus of claim 8, further comprising an elongated member at least partially within said first channel, wherein said elongated member contacts said portion of said bone-engaging member in said first channel.

10. The apparatus of claim 1, wherein said engaging portion and said shaft portion are unitary with each other.

11. The apparatus of claim 1, wherein said receiver member is a one-piece member.

12. The apparatus of claim 1, wherein said vertical axis is centered along said first channel, and wherein said opening is laterally offset from said vertical axis and does not intersect said vertical axis.

13. The apparatus of claim 1, wherein said longitudinal axis of said second channel is substantially parallel with said vertical axis.

14. The apparatus of claim 13, wherein said longitudinal axis of said second channel is parallel with said vertical axis.

15. The apparatus of claim 1, wherein said opening extends between said first and second channels along a horizontal axis arranged substantially perpendicular to said vertical axis.

16. An apparatus comprising:

a receiver member extending along a vertical axis and having two branches, a base portion, a first channel substantially between said branches and including an arcuate bottom surface for receiving an elongated member, a second channel for receiving a bone-engaging member, said second channel being non-collinear with said first channel and having a longitudinal axis, and an opening extending transversely to said vertical axis through a portion of said arcuate bottom surface and between said first channel and said second channel;

a bone-engaging member having an engaging portion and a shaft portion that are substantially collinear, said shaft portion being at least partially within said second channel; and a lock member connected to said receiver member, wherein said apparatus has a locked condition in which said receiver member and said bone-engaging member are substantially immobile with respect to each other, and an unlocked condition in which said bone-engaging member and said receiver member are movable with respect to each other around and along said second channel to an infinite number of relative positions; and wherein said first channel has a longitudinal axis, said vertical axis is perpendicular to said axis of said first channel, and said axis of said second channel is substantially parallel to said vertical axis.

17. The apparatus of claim 16, wherein said receiver member includes a force-transmitting member in said opening.

18. The apparatus of claim 17, further comprising an elongated member at least partially within said first channel, wherein said force-transmitting member is at least partially within said first channel, and wherein said elongated member contacts said force-transmitting member in said first channel and presses said force-transmitting member against said bone-engaging member.

19. The apparatus of claim 16, wherein said vertical axis is centered along said first channel, and wherein said opening is laterally offset from said vertical axis and does not intersect said vertical axis.

20. The apparatus of claim 16, wherein said longitudinal axis of said second channel is parallel with said vertical axis.

21. The apparatus of claim 16, wherein said opening extends between said first and second channels along a horizontal axis arranged substantially perpendicular to said vertical axis.

22. The apparatus of claim 16, wherein each of said branches of said receiver member has a length extending along said vertical axis, said second channel extending along said vertical axis and through one of said branches along said length from a top surface of said one of said branches to an opposite bottom surface of said base portion.

23. An apparatus comprising: a receiver member extending along a vertical axis and having two branches, a base portion, a first channel substantially between said branches and including an arcuate bottom surface for receiving an elongated member, a second channel for receiving a bone-engaging member, said second channel being non-collinear with said first channel and having a longitudinal axis, and an opening extending transversely to said vertical axis through a portion of said arcuate bottom surface and between said first channel and said second channel; a bone-engaging member having an engaging portion and a shaft portion that are substantially collinear, said shaft portion being at least partially within said second channel; and a lock member connected to said receiver member, wherein said apparatus has a locked condition in which said receiver member and said bone-engaging member are substantially immobile with respect to each other, and an unlocked condition in which said bone-engaging member and said receiver member are movable with respect to each other around and along said second channel to an infinite number of relative positions; and wherein said first channel has a longitudinal axis, said vertical axis is perpendicular to said axis of said first channel, and said axis of said second channel is substantially parallel and laterally offset from said vertical axis said vertical axis.

24. An apparatus comprising:

a receiver member extending along a vertical axis and having two branches each having a length extending along said vertical axis, a base portion, a first channel defined between said branches and including an arcuate bottom surface for receiving an elongated support member, a second channel offset from said first channel and extending along said vertical axis and through one of said branches along said length from a top surface of said one of said branches to an opposite bottom surface of said base portion, and an opening extending transversely to said vertical axis through a portion of said arcuate bottom surface and between said first channel and said second channel;

a bone-engaging member having an integral shaft portion and engaging portion, said shaft portion being at least partially within said second channel; and a lock member connected to said receiver member.

25. The apparatus of claim 24, further comprising an elongated member at least partially within said first channel.

26. The apparatus of claim 24, wherein said bone-engaging member includes a threaded portion.

27. The apparatus of claim 24, wherein said lock member is a set screw.

28. The apparatus of claim 24, wherein said shaft portion and said engaging portion are immovable with respect to each other during implantation of said bone-engaging member in bone.

29. The apparatus of claim 24, wherein said vertical axis is centered along said first channel, and wherein said opening is laterally offset from said vertical axis and does not intersect said vertical axis.

30. The apparatus of claim 24, wherein said longitudinal axis of said second channel is substantially parallel with said vertical axis.

31. The apparatus of claim 24, wherein said opening extends between said first and second channels along a horizontal axis arranged substantially perpendicular to said vertical axis.

* * * * *

UNITED STATES PATENT AND TRADEMARK OFFICE
CERTIFICATE OF CORRECTION

PATENT NO. : 7,850,716 B2  
APPLICATION NO. : 11/357767  
DATED : December 14, 2010  
INVENTOR(S) : Taylor Page 1 of 1

It is certified that error appears in the above-identified patent and that said Letters Patent is hereby corrected as shown below:

On the Face Page, in Field (56), under "U.S. PATENT DOCUMENTS", in Column 1, Line 1, delete "Harms" and insert -- Harms et al. --, therefor.

On the Face Page, in Field (56), under "U.S. PATENT DOCUMENTS", in Column 1, Line 2, delete "Errico" and insert -- Errico et al. --, therefor.

On the Face Page, in Field (56), under "U.S. PATENT DOCUMENTS", in Column 1, Line 3, delete "Errico" and insert -- Errico et al. --, therefor.

On the Face Page, in Field (56), under "U.S. PATENT DOCUMENTS", in Column 2, Line 2, delete "Sherman" and insert -- Sherman et al. --, therefor.

On the Face Page, in Field (56), under "U.S. PATENT DOCUMENTS", in Column 2, Line 5, delete "Metz-Stavenhagen" and insert -- Metz-Stavenhagen et al. --, therefor.

On the Face Page, in Field (56), under "U.S. PATENT DOCUMENTS", in Column 2, Line 6, delete "Barker" and insert -- Barker et al. --, therefor.

On the Face Page, in Field (56), under "U.S. PATENT DOCUMENTS", in Column 2, Line 7, delete "Taylor" and insert -- Taylor et al. --, therefor.

In Column 11, Line 11, in Claim 23, after "from", delete "said vertical axis".

Signed and Sealed this  
Twenty-sixth Day of April, 2011

David J. Kappos  
*Director of the United States Patent and Trademark Office*